United States Patent [19]

Nakajima et al.

[11] 4,247,632

[45] Jan. 27, 1981

[54] METHYLGUANIDINE-DECOMPOSING ENZYME AND PROCESS FOR ITS PRODUCTION

[75] Inventors: Motoo Nakajima; Kiyoshi Mizusawa; Yoshio Shirokane, all of Noda, Japan

[73] Assignee: Kikkoman Shoyu Co., Ltd., Noda, Japan

[21] Appl. No.: 37,028

[22] Filed: May 8, 1979

[30] Foreign Application Priority Data

May 16, 1978 [JP] Japan .................................. 53-57217
Dec. 26, 1978 [JP] Japan ................................ 53-159296
Feb. 28, 1979 [JP] Japan .................................. 54-21967
Mar. 19, 1979 [JP] Japan .................................. 54-31171

[51] Int. Cl.$^3$ .......................... C12Q 1/58; C12N 9/78
[52] U.S. Cl. ........................................ 435/12; 435/15; 435/18; 435/227; 435/232; 435/829; 435/267; 435/269; 435/268; 426/56

[58] Field of Search ............... 435/195, 227, 232, 829, 435/12, 15, 267–269; 426/56

[56] References Cited

PUBLICATIONS

Enzyme Nomenclature (1972), published Elsevier 1973, pp. 256–258 (3.5.3 in Linear Amidines).

*Primary Examiner*—Lionel M. Shapiro
*Attorney, Agent, or Firm*—Schuyler, Banner, Birch, McKie & Beckett

[57] ABSTRACT

A novel methylguanidine-decomposing enzyme can be obtained by cultivating in a medium a bacterium belonging to Genus Alcaligenes and having an ability to produce a methylguanidine-decomposing enzyme. This methylguanidine-decomposing enzyme has an ability to decompose methylguanidine into methylamine and urea. Its optimum pH range is 10.9–12.3 and its stable pH range is 5.0–10.6.

11 Claims, 11 Drawing Figures

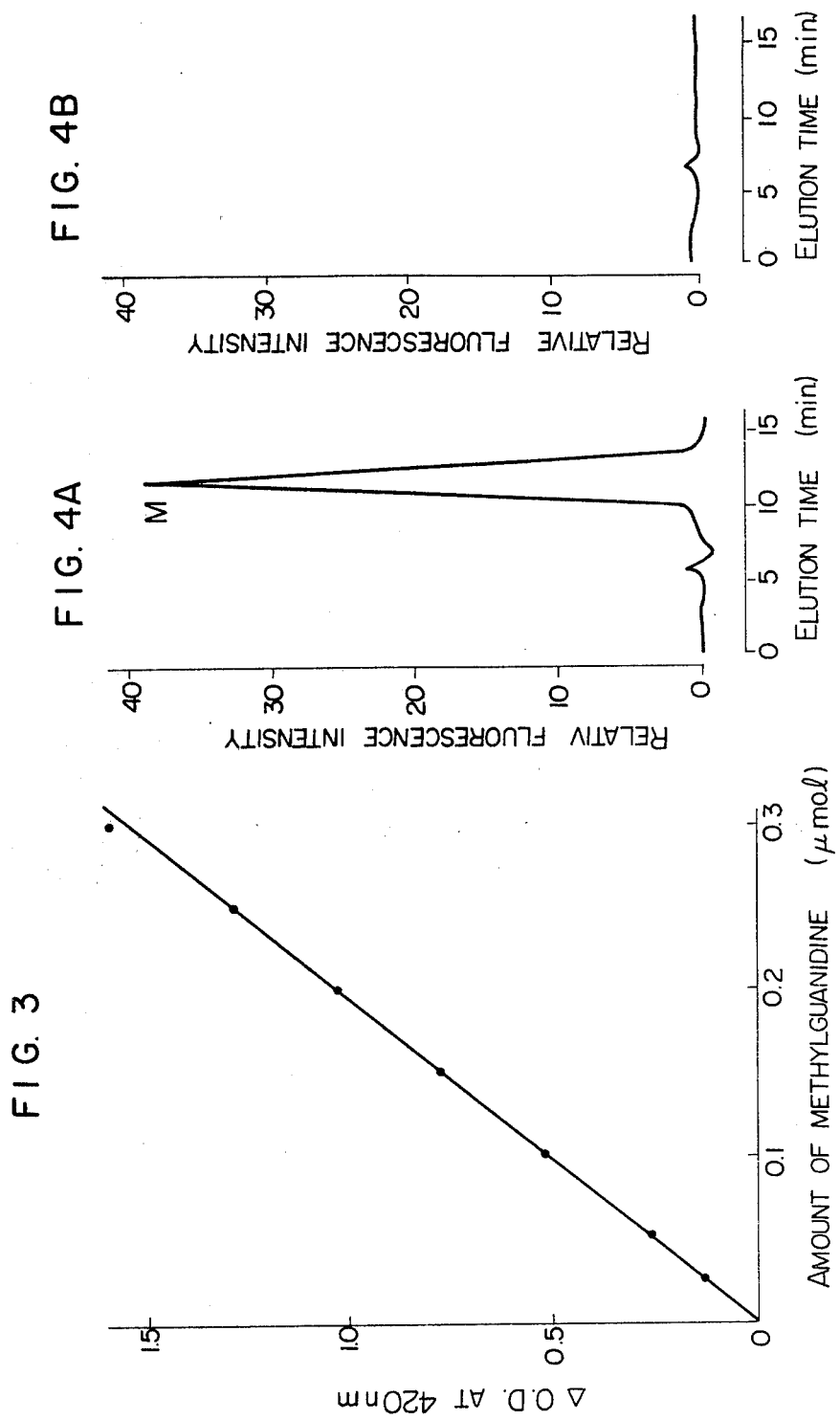

METHYLGUANIDINE-DECOMPOSING ENZYME AND PROCESS FOR ITS PRODUCTION

This invention relates to a novel methylguanidine-decomposing enzyme. More particularly, this invention relates to a novel methylguanidine-decomposing enzyme which decomposes methylguanidine into methylamine and urea, as well as to process for producing said enzyme and the use of said enzyme.

Methylguanidine is contained in foodstuffs such as smoked-dried bonito (Katsuo-bushi), meat extract and the like in considerable quantities. It is said that the methylguanidine is easily converted by nitrosation to methylnitrosocyanamide in the gastric juice in the presence of a nitrite and that said methylnitrosocyanamide is a strongly mutagenic substance. It is sometimes referred to as a carcinogen.

Though methylguanidine is hardly detected in the blood of normal human, it is detected in the blood of the patients with chronic renal failure and said to be a sort of uremic toxin causing uremia. It is also known that the in vitro toxicity of methylguanidine involves LDH inhibition, ATPase inhibition, inhibition of oxidative phosphorylation, inhibition of platelet factor 3, etc. [Ando et al.: Saishin Igaku, 31, No. 9, pp. 1695–1706 (1976)].

In view of the actual state of the matter mentioned above, the present inventors have conducted earnest studies about the method for decomposing methylguanidine, known as a substance exercising various undesirable effects on human body, into harmless substances and removing it. As the result, it has been found that a bacterium belonging to Genus Alcaligenes, isolated from soil, produces a methylguanidine-decomposing enzyme which decomposes methylguanidine into harmless methylamine and urea and of which action has not been known hitherto at all. It has been also found that, if said methylguanidine-decomposing enzyme is allowed to act upon a sample to be analyzed for methylguanidine content and the amount of methylamine or urea formed is measured, methylguanidine can be analyzed quantitatively by a very simple procedure in a very short period of time with a very high sensitivity and a large number of samples can be analyzed simultaneously. Based on these findings, this invention has been accomplished.

According to this invention, there are provided (1) a methylguanidine-decomposing enzyme having an ability to decompose methylguanidine into methylamine and urea of which optimum pH range is 10.9–12.3 and of which stable pH range is 5.0–10.6, (2) a process for removing methylguanidine from a sample containing methylguanidine which comprises adding said methylguanidine-decomposing enzyme to a sample containing methylguanidine and enzymatically decomposing the methylguanidine, (3) a method for quantitatively analyzing methylguanidine present in a sample which comprises reacting a methylguanidine-decomposing enzyme with a sample to be analyzed for methylguanidine content and measuring the quantity of methylamine or urea formed by the reaction, and (4) a process for producing a methylguanidine-decomposing enzyme which comprises cultivating a bacterium belonging to Genus Alcaligenes and having an ability to produce a methylguanidine-decomposing enzyme in a medium and collecting the formed methylguanidine-decomposing enzyme from the cultivated mixture.

It is an object of this invention to provide a novel methylguanidine-decomposing enzyme.

It is another object of this invention to provide a novel process for removing methylguanidine from a sample containing methylguanidine.

It is yet another object of this invention to provide a novel method for quantitatively analyzing methylguanidine in a sample containing methylguanidine.

It is still another object of this invention to provide a novel process for producing a methylguanidine-decomposing enzyme.

Other objects and advantages of this invention will be apparent from the descriptions given below.

In the accompanying drawings,

FIG. 1 is a graph depicting the optimum pH range of methylguanidine-decomposing enzyme prepared by cultivating a strain Alcaligenes N-81 or Alcaligenes N-243, wherein the measurement was carried out by using methylguanidine as a substrate;

FIG. 2 (standard calibration curve) is a graph illustrating the correlation between the quantity of methylguanidine and O.D. value measured by urease-indophenol method; and FIG. 3 (standard calibration curve) is a graph illustrating the correlation between the quantity of methylguanidine and O.D. value measured by T. N. B. S. method.

FIG. 4A illustrates the liquid chromatogram of a solution of methylguanidine sulfate in 0.1 M Trishydrochloric acid buffer (before the enzymatic reaction), wherein M is the peak of methylguanidine.

FIG. 4B illustrates the liquid chromatogram of an enzyme-treated product obtained by reacting a methylguanidine-decomposing enzyme with a solution of methylguanidine sulfate in 0.1 M Tris-hydrochloric acid buffer (after the enzymatic reaction).

This invention will be explained in detail below.

First of all, the physical and chemical properties of the methylguanidine-decomposing enzyme of this invention will be mentioned.

(1) Action

This enzyme decomposes methylguanidine to form methylamine and urea:

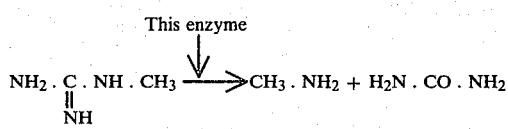

$$NH_2 \cdot \underset{\underset{NH}{\|}}{C} \cdot NH \cdot CH_3 \xrightarrow{\text{This enzyme}} CH_3 \cdot NH_2 + H_2N \cdot CO \cdot NH_2$$

(2) Substrate specificity

This enzyme exerts no action upon guanidoacetic acid (glycocyamine) and guanididosuccinic acid.

(3) Optimum pH and stable pH ranges

Figure 1:
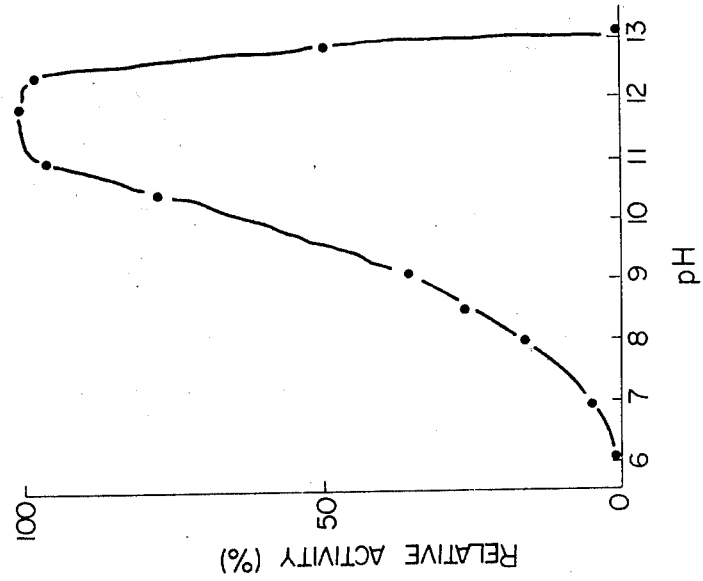

As shown in FIG. 1, its optimum pH range is 10.9-12.3 and its stable pH range is 5.0-10.6 when reacted with methylguanidine suflate, as a substrate, at 30° C. for 10 minutes, wherein the following buffer solutions were used in the following pH ranges: pH 6.0-7.0:0.1 M citric acid buffer solution; pH 7.0-9.0:0.1 M Veronal buffer solution; pH 9.0-11.0:0.1 M sodium carbonate-sodium bicarbonate buffer solution; pH 11.0-13.5:0.1 M sodium carbonate-sodium hydroxide buffer solution.

(4) Method for measuring the enzymatic activity

A substrate solution having a methylguanidine sulfate concentration of 100 µg/ml is prepared by dissolving methylguanidine sulfate into 0.05 M sodium carbonate-sodium bicarbonate buffer solution (pH 11.0). 0.8 ml of the substrate solution is allowed to react with 0.2 ml of enzyme solution at 30° C. for 10 minutes, and then the reaction is stopped by adding 1 ml of 0.4 M solution of trichloroacetic acid thereto. If a precipitate is formed, the precipitate is removed by centrifugation or filtration. Thus, an enzymatic reaction fluid is obtained.

A control is prepared by repeating all the same procedure as above, except that the 0.2 ml of enzyme solution is replaced by 0.2 ml of 0.05 M sodium carbonate-sodium bicarbonate buffer solution (pH 11.0).

Then, each 50 µl of the enzymatic reaction fluid or the control is mixed with 1.5 ml of 0.1 mM solution of phenanthraquinone in dimethylformamide and 0.25 ml of 1 M aqueous solution of sodium hydroxide and subjected to reaction at room temperature for 40-50 minutes, and then 0.25 ml of concentrated hydrochloric acid and 2.5 ml of water are added. Then, the relative fluorescence intensities of the resulted reaction mixtures are measured with a fluorophotometer at an exciting wave length of 310 nm and a fluorescence wave length of 390 nm. The decrease in methylguanidine content is calculated from the difference in fluorescence intensities between each reaction mixture for the enzymatic reaction and the control.

In the expression of activity, a quantity of enzyme enough to decompose 1 µ-mole of methylguanidine per 1 minute at 30° C. is defined as one unit.

(5) Optimum action temperature range

When this enzyme is allowed to act at pH 10 for 10 minutes, its optimum action temperature is in the range of 20°-75° C. Particularly, the temperature range of 55°-60° C. is best.

(6) Inactivating pH and temperature conditions (i) Inactivating pH condition

This enzyme is completely inactivated below pH 3 and above pH 13.

(ii) Inactivating temperature condition

At pH 10, this enzyme is completely inactivated by a heat treatment effected at 60° C. for 30 minutes.

(7) Inhibition, activation and stabilization (i) Inhibition (a) Addition of mercurie chloride or silver nitrate The residual activity of enzyme after a treatment at 30° C. at pH 10 for 60 minutes in the presence of 1 mM of HgCl₂ or AgNO₃ is shown in Table 1, wherein the activity in the absence of inhibitor is taken as 100.

(b) Addition of potassium cyanamide, ethylenediaminetetraacetate, iodine, dithiothreitol or 2-mercaptoethanol.

The residual activity of enzyme after a treatment at 30° C. at pH 9 for 6 hours in the presence of 50 mM of KCN, the residual activity of enzyme after a treatment at 40° C. at pH 10 for 4 hours in the presence of 100 mM of ethylenediaminetetraacetate, the residual activity of enzyme after a treatment at 40° C. at pH 7 for 1 hour in the presence of 1 mM of I₂ and the residual activity of enzyme after a treatment at 30° C. at pH 9 for 1 hour in the presence of 1 mM of dithiothreitol or 2-mercaptoethanol are shown in Table 1, wherein the activity of enzyme in the absence of inhibitor is taken as 100.

TABLE 1

| Inhibitor added | Concentration of inhibitor (mM) | Residual activity of enzyme (%) |
|---|---|---|
| HgCl₂ | 1 | 0 |
| I₂ | 1 | 0 |
| Dithiothreitol | 1 | 0 |
| 2-Mercaptoethanol | 1 | 0 |
| KCN | 50 | 0 |
| Ethylenediaminetetraacetate | 100 | 0 |
| AgNO₃ | 1 | 4 |

As is shown in Table 1, the enzyme is markedly inhibited by HgCl₂, I₂, dithiothreitol, 2-mercaptoethanol, KCN, ethylenediaminetetraacetate and AgNO₃.

(ii) Activation

There is not yet found any reagent particularly activating the enzyme.

(iii) Stabilization

The enzyme is stabilized by adding 10% (V/W) of glycerin to it.

(8) Method of purification

Wet bacterial cells are collected by centrifuging the cultivated mixture. After the bacterial cells are suspended in 0.05 M Veronal buffer solution (pH 9.0), the cells are destructed by means of an ultrasonic disintergrator while cooling with ice water.

Then, the precipitate is removed by centrifugation and the supernatant (crude enzyme solution) is taken.

Then, it is salted out with ammonium sulfate in usual manner, and the precipitate formed at 55% saturation is separated by centrifugation. The precipitate is dissolved into a small quantity of 0.01 M Tris-hydrochloric acid buffer (pH 8.0). The resulting solution is subjected to a gel filtration chromatography by passing it through a column of Sephadex G-200 previously equilibrated with a 0.1 M solution of potassium chloride (KCl) in 0.01 M Tris-hydrochloric acid buffer (pH 8.0).

The active fraction thus obtained is passed through a column of DEAE-Sephacel previously equilibrated with the above-mentioned 0.01 M Tris-hydrochloric acid buffer solution containing KCl, and then it is subjected to ion-exchange chromatography first (till the volume of eluate reaches 120 ml) with the abovementioned 0.01 M Tris-hydrochloric acid buffer solution containing KCl and thereafter by the concentration gradient elution method using 0.2-0.4 M KCl.

The active fraction thus obtained is adsorbed onto a column packed with hydroxyappatite. Till the volume of eluate reaches 200 ml, it is eluted with the above-mentioned 0.01 M Tris-hydrochloric acid buffer solution containing KCl. Thereafter, it is eluted with phosphate buffer solution (pH 8.0) of which concentration is stepwise elevated from 0.001 M to 0.005 M, 0.01 M, 0.03 M, 0.05 M and 0.07 M. Finally, it is eluted with 0.1 M phosphate buffer solution (pH 8.0) to collect the active fraction of this enzyme.

The active fraction thus obtained is dialyzed against deionized water, after which it is freeze-dried to give a purified powder of this enzyme.

An electrophoretic measurement by the use of polyacrylamide gel has revealed that this purified enzyme is uniform electrophoretically.

(9) Molecular weight

This enzyme has a molecular weight of about 225,000±9,000 as measured by the method of Hedrick and Smith [J. L. Hedrick and A. J. Smith: Archives of Biochemistry and Biophysics, 126, 155-164 (1968)].

Up to today, there has been found no enzyme capable of decomposing methylguanidine to form methylamine and urea. Therefore, the methylguanidine-decomposing enzyme obtainable by this invention is a novel enzyme. If methylguanidine-containing drinks and foods exercising harmful effects on human body are treated with this enzyme, the methylguanidine can readily be decomposed into harmless substances and removed, so that the safety of drinks and foods can be enhanced by this enzyme treatment to a great extent. It is possible, moreover, to develop new applications of this enzyme such as a reagent for treating uremia or as biochemical reagents. Thus, this invention is quite meaningful from the industrial point of view.

Next, here will be mentioned the process for removing methylguanidine from methylguanidine-containing samples by adding the above-mentioned methylguanidine-decomposing enzyme to a methylguanidine-containing sample and enzymatically decomposing the methylguanidine.

First, the pretreatment of methylguanidine-containing sample, which is carried out before reacting a methylguanidine-decomposing enzyme with the methylguanidine-containing sample, will be mentioned.

As the methylguanidine-containing sample constituting the object, any substances may be selected so far as they contain methylguanidine. Their examples include extracts of chicken, beef, whale meat, pork, fish meat and the like; foodstuffs such as smoked-dried bonito (Katsuo-bushi), smoked-dried mackerel (Saba-bushi), smoked-dried round herring (Urume-bushi) and the like; and the blood of uremic patients.

Among the above-mentioned methylguanidine-containing substances, meat extracts are used either directly or after being diluted to an appropriate concentration with a solvent usable in food processing such as water, alcohol, water-alcohol mixture, emulsion, seasoning solution or the like.

The smoked-dried fishes are used, for example, in the form of extract obtainable by extracting, with cold water, hot water or the like, the smoked-dried fishes either directly or after pulverizing or slicing them with conventional pulverizer or slicer and then, if necessary, homogenizing them with conventional homogenizer or the like.

The blood is used either as it is or after being diluted to an appropriate concentration with physiological salt solution.

pH of the above-mentioned methylguanidine-containing substances may not be regulated. Preferably, however, it is adjusted to 5-12 and particularly 6-10 in the case of the above-mentioned meat extracts or foodstuffs such as smoked-dried fishes and to 7.2-7.6 and particularly about 7.4 in the case of blood, by means of an appropriate pH adjustment reagent such as hydrochloric acid, sodium hydroxide or the like.

In acting upon the above-mentioned methylguanidine-containing substances, the amount of methylguanidine-decomposing enzyme added is appropriately varied with consideration of methylguanidine content in the methylguanidine-containing substance and conditions of the reaction.

The temperature at which a methylguanidine-containing substance is decomposed with methylguanidine-decomposing enzyme is 80° C. or below and preferably 20°-60° in the case of meat extract or foodstuffs such as smoked-dried fishes, while it is 50° C. or below and preferably 35°-40° C. in the case of blood. At the above-mentioned temperature, the methylguanidine-containing substances are allowed to stand or stirred for an appropriate period of time during which they undergo an enzymatic reaction to yield a harmless enzymatic decomposition product.

After methylguanidine has been decomposed and removed from a methylguanidine-containing substance as above, it is allowable, if necessary, to inactivate the enzyme by a disclosed means such as heating, separate or remove and then to adjust pH of the product to an appropriate value with hydrochloric acid, sodium hydroxide or the like.

Further, the solvent used in the enzymatic reaction is separated and removed in the usual manner, if necessary.

As above, methylguanidine can be separated and removed completely from a foodstuff containing methylguanidine, so that the safety of the foodstuff can be enhanced to a great extent. Further, it is possible to decompose methylguanidine present in the blood of uremic patient, exercising a harmful effect on human body, and to remove it from the blood completely.

Next, here will be mentioned a method for quantitatively analyzing methylguanidine in a sample by reaction of the above-mentioned methylguanidine-decomposing enzyme with a sample to be analyzed for methylguanidine and measuring the quantity of methylamine or urea formed by the reaction.

The sample to be quantitatively analyzed for methylguanidine may be any substance so far as it contains methylguanidine. Examples of said sample include meat extracts, foodstuffs such as smoked-dried fishes, bloods, sera, urines and the like.

In analyzing methylguanidine in the above-mentioned smoked-dried fishes, there is employed, for example, an extract obtainable by extracting the smoked-dried fishes with cold water, hot water ot the like either directly or after pulverizing or slicing them by means of pulverizer or slicer and then, if necessary, homogenizing them by means of a homogenizer or the like.

pH of the above-mentioned samples may not be regulated. Preferably, however, they are adjusted to pH 5-12 and particularly pH 9-11 by means of an appropriate pH adjustment reagent such as hydrochloric acid, sulfuric acid, nitric acid, sodium hydroxide, potassium hydroxide or the like.

The above-mentioned samples are used for the quantitative analysis either directly or after being diluted to an appropriate concentration with water, a buffer solution or the like.

Then, a methylguanidine-decomposing enzyme is allowed to react with the sample prepared as above to decompose the latter into methylamine and urea.

When a sample to be analyzed for methylguanidine is allowed to react with methylguanidine-decomposing enzyme, the amount of the enzyme added may be appropriately varied with consideration of the methylguanidine content of the sample to be analyzed for methylguanidine and the conditions of the reaction.

The temperature at which the sample is decomposed with methylguanidine-decomposing enzyme is 80° C. or below and preferably 20°-60° C. At said temperature, the enzyme is added to the sample and the mixture is allowed to stand or stirred for an appropriate period of time during which it undergoes an enzymatic reaction and the methylguanidine is decomposed into methylamine and urea enzymatically.

Subsequently, the content of methylamine or urea in the enzymatic decomposition product is determined by disclosed method.

When the sample to be reacted with methylguanidine-decomposing enzyme beforehand contains methylamine, urea or their analogous compounds, their initial content measured previously by disclosed method is deducted from the content of methylamine or urea measured after the above-mentioned enzymatic decomposition reaction.

As the method for determining methylamine, any method may be employed. The methods employable include, for example, (1) the method which comprises reacting methylamine with an alkaline aqueous solution of T.N.B.S. (sodium 2,4,6-trinitrobenzenesulfonate) and colorimetrically determining it at 420 nm (T.N.B.S. method) [T. Okuyama et al.: J. Biochem. 47, 454 (1960)]; (2) the method which comprises reacting methylamine with ninhydrin reagent in a citric acid buffer solution (pH 5) at an elevated temperature and then colorimetrically determining it at 570 nm [E. Yemm et al.: Analyst, 80, 209 (1955)]; and (3) the method which comprises reacting a primary amine with o-phthalaldehyde and measuring the intensity of the fluorescence at an exciting wave length of 340 nm and a fluorescence wave length of 455 nm [M. Roth: Anal. Chem., 43, 880 (1971)].

As the method for determining urea, any method may be employed. The methods employable include, for example, (1) the method which comprises decomposing urea with urease into ammonia and carbon dioxide and colorimetrically determining the ammonia by Berthelot reaction (indophenol reaction) (urease-indophenol method) [R. L. Searcy and F. M. Cor: Clin. Chim. Acta, 8, 810 (1963)]; (2) the method which comprises decomposing urea with urease into ammonia and carbon dioxide and colorimetrically determining the ammonia by Nessler reaction (urease-Nessler method) [M. Saito, T. Uchida, E. Suzuki: Rinsho Kensa, 8, 878 (1964)]; and (3) the method which comprises heating urea in the presence of diacetyl monoxime in an acidic solution to develop a yellow color and then colorimetrically determining the yellow color (Fearon method) [W. R. Fearon: Biochem. J., 33, 902 (1939)].

Next, it is necessary to determine the correlation between the quantity of methylamine or urea and the O.D. value and prepare a calibration curve on the basis of the correlation. Thus, the following experiments were carried out in order to study the correlation between the quantity of methylguanidine in sample and O.D. value.

EXPERIMENTAL EXAMPLE 1

Determination of Urea by Urease-Indophenol Method

I. Preparation of Reagents (1) Methylguanidine-decomposing enzyme solution 2 liters of a medium (pH 7.2) comprising 1.0% (W/V) of glycerin, 0.2% (W/V) of methylguanidine sulfate, 0.1% (W/V) of disodium phosphate, 0.1% (W/V) of magnesium sulfate, 0.05% (W/V) of yeast extract, 0.01% (W/V) of ferrous sulfate, 0.01% (W/V) of manganese chloride and water was introduced into the cultivating vessel of a small-sized jar fermenter (manufactured by Iwashiya) and sterilized in an autoclave. The medium was inoculated with 20 ml of seed culture of Alcaligenes N-243 (FERM-P No. 4369, ATCC 31370) which had been cultivated for 48 hours in a medium (pH 7.2) having the same composition as above. It was subjected to aeration spinner submerged culture at 30° C. for 48 hours.

The culture fluid thus obtained was centrifuged to give 17 g of wet bacterial cells, and the resulting cells were suspended in 50 ml of 0.05 M Veronal buffer solution (pH 9.0), and the cells were destructed by means of an ultrasonic disintegrator (manufactured by Bronson Co.) for 10 minutes while cooling with ice water.

Then the precipitate was removed by centrifugation, and there was obtained 48 ml of supernatant (crude enzyme solution) (enzyme activity: 43.3 units/ml).

The crude enzyme solution was salted out with ammonium sulfate in the usual manner. The resulting precipitate fraction was dissolved into 25 ml of water and dialyzed against 0.05 M Tris-hydrochloric acid buffer solution (pH 8.0) to give a methylguanidine-decomposing enzyme solution (enzyme activity: 60.5 units/ml).

(2) Reagent A (Urease buffer solution)

40 mg of urease (type IX, manufactured by Sigma Co.) and 200 mg of EDTA-2Na were dissolved into 20 ml of 50 mM phosphate buffer solution (pH 6.5).

(3) Reagent B (Phenol reagent)

5.0 g of phenol and 25 mg of sodium nitroprusside were dissolved into distilled water and the volume was adjusted to 500 ml.

(4) Reagent C (Alkaline hypochlorite reagent)

2.5 g of sodium hydroxide and 2.5 ml of sodium hypochlorite solution having an effective chlorine concentration of 5% were dissolved into distilled water and the volume was adjusted to 500 ml.

II. Determination of Urea formed from Methylguanidine

Methylguanidine sulfate was dissolved into 0.05 M sodium carbonate-sodium bicarbonate buffer solution (pH 10.0) so that the amount of methylguanidine became 0, 0.01, 0.02, 0.04, 0.06, 0.08 or 0.10 micromole. Each 90 μl of the solution thus obtained was thoroughly mixed with 10 μl of the above-mentioned methylguanidine-decomposing enzyme and the mixture was reacted at 37° C. for 30 minutes while it was left standing.

Then, 100 μl of 0.2 M phosphate buffer solution and then 200 μl of reagent A were added to the enzymatic reaction product thus obtained. The resulting mixture was thoroughly stirred and then reacted at 37° C. for 20 minutes while it was left standing.

To the reaction product thus obtained were added 5 ml of reagent B and 5 ml of Reagent C. The resulting mixture was immediately vigorously stirred and then left standing at 37° C. for 15 minutes, and then the color was determined with a colorimeter at 625 nm.

The blank was measured by repeating just the same procedure as above, except that 10 μl of the above-mentioned methylguanidine-decomposing enzyme solution was treated in a boiling water bath at 100° C. for 5 minutes, then it was added to 90 μl of 0.05 M sodium carbonate-sodium bicarbonate buffer solution (pH 10.0), the resulting mixture was thoroughly stirred and reacted at 37° C. for 30 minutes while it was left standing.

Figure 2:
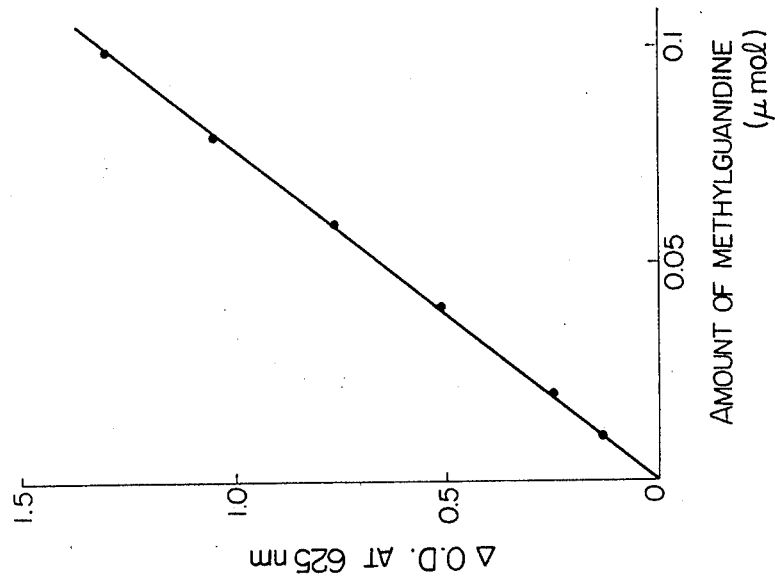

The value of blank was deducted from the O.D. value for each mixture. The correlation between the O.D. value after the deduction and the quantity of methylguanidine is shown in FIG. 2. FIG. 2 clearly demonstrates that there is a linear correlation between the quantity of methylguanidine and the O.D. value after the deduction so that the correlation can satisfactorily be used as a standard calibration curve.

EXPERIMENTAL EXAMPLE 2

Determination of Methylamine by T.N.B.S. Method

Methylguanidine sulfate was dissolved into 0.1 M sodium carbonate-sodium bicarbonate buffer solution (pH 10.0) so that the amount of methylguanidine sulfate became 0, 0.01, 0.02, 0.05, 0.1, 0.15, 0.2, 0.25 or 0.3 micromole. Each 900 μl of the solution thus obtained was uniformly mixed with 100 μl of the same enzyme solution as mentioned in Experimental Example 1. The resulting mixture was reacted at 37° C. for 30 minutes, while it was left standing.

To the enzymatic reaction product thus obtained was added 2 ml of 0.1 M borax-sodium hydroxide buffer solution (pH 9.6) to stop the enzymatic reaction. Then 1 ml of 0.4% aqueous solution of T.N.B.S. was added, the resulting mixture was thoroughly stirred, and it was reacted at 37° C. for exactly 23 minutes, and then its color was colorimetrically measured at 420 nm.

The above-mentioned color-forming reaction was carried out by means of a discrete automated analyzer (type AC-60, manufactured by Pye Unican Co., Ltd.).

The blank was measured by repeating just the same procedure as above, except that 100 μl of the same methylguanidine-decomposing enzyme solution as mentioned in Experimental Example 1 was treated in a boiling water bath at 100° C. for 5 minutes, it was uniformly mixed with 900 μl of 0.1 M sodium carbonate-sodium bicarbonate buffer solution (pH 10.0), and the mixture was reacted at 37° C. for 30 minutes while it was left standing.

The value of blank was deducted from the O.D. value for each mixture. The correlation between the O.D. value after the deduction and the quantity of methylguanidine is shown in FIG. 3. FIG. 3 clearly demonstrates that there is a linear correlation between the quantity of methylguanidine and the O.D. value after the deduction so that the correlation can satisfactorily be used as a standard calibration curve.

If the O.D. value obtained for methylamine or the O.D. value obtained for urea, measured in the above-mentioned manner, is applied to the standard calibration curve based on methylamine or to the standard calibration curve based on urea, the quantity of methylguanidine in sample can be determined.

This invention is quite valuable from the industrial point of view in that the procedure is quite simple as compared with disclosed processes, the time period necessary for measuring one sample is greatly shortened as compared with disclosed processes, it is quite excellent in sensitivity, and it enables to measure a large number of samples simultaneously.

Hereunder will be mentioned the concrete process for producing the methylguanidine-decomposing enzyme according to this invention.

The bacteria used in this invention may be any bacteria so far as they belong to Genus Alcaligenes and have an ability to produce a methylguanidine-decomposing enzyme. Varieties or mutant strains of these bacteria may also be used. Concrete examples of the bacteria belonging to Genus Alcaligenes and having an ability to produce a methylguanidine-decomposing enzyme include Alcaligenes N-81, Alcaligenes N-243 and the like.

Both Alcaligenes N-81 and Alcaligenes N-243 are bacteria which the present inventors have newly isolated from soil. Their bacteriological properties are as shown below. Most of the bacteriological properties have been revealed according to the methods mentioned in Manual of Microbiological Methods (1959, published by McGraw-Hill Book Co.).

Bacteriological Properties of Alcaligenes N-81

(a) Morphology

Microscopic observation (cultured in a bouillon-agar medium at 30° C. for 48 hours)

(1) Shape and size of cell: It is a short rod having a size of 1–2×0.5 micron.
(2) Polymorphism of the cell: There is observed no polymorphism.
(3) Motility: Motile by means of one to several peritrichous flagella.
(4) Spore: It forms no spore.
(5) Gram-stain: Negative.
(6) Acid-fast: Negative.

(b) The State of Growth in Various Media:

(1) Bouillon-agar plate culture
   Circular colonies having a diameter of 1–2 mm are formed when cultivated at 30° C. for 48 hours. The surface is flat and has convex round protrusions. The periphery is all-round. The colonies assume yellow with a gloss.
(2) Bouillon-agar slant culture
   It shows a stringy medium growth when cultivated at 30° C. for 48 hours. The surface is flat with yellow color and gloss.
(3) Bouillon submerged culture
   In a standing culture at 30° C. for 48 hours, it forms slight turbidity with sediments.
(4) Bouillon-gelatin stab culture
   In standing culture at 20° C. for 42 days, it grows up to about 1 cm from the surface of medium without liquefaction of gelatin.
(5) Litmus milk culture
   In a standing culture at 30° C. for 14 days, the medium becomes a little alkaline without coagulation of litmus milk.

(c) Physiological properties (1) Reduction of nitrates: Observed.
(2) Denitrification reaction: Slightly observed.
(3) MR test: Negative.
(4) VP test: Negative.
(5) Formation of indole: Not observed.
(6) Formation of hydrogen sulfide: Not observed.
(7) Hydrolysis of starch: Not observed.
(8) Utilization of citric acid: Observed. (Christensen medium is used.)

(9) Inorganic nitrogen source: Utilized. (Nitrates, ammonium salts)
(10) Formation of pigment: Not observed.
(11) Urease: Positive.
(12) Catalase: Negative.
(13) Growing condition range:
Temperature: 15°–40° C.
pH: 6–10
(14) Behavior to oxygen: Aerobic.
(15) O-F test (Hugh Leifson method): Negative.
(16) Utilization of carbon sources:
Carbon sources such as L-arabinose, D-xylose, D-glucose, D-mannose, D-fructose, D-galactose, maltose, sucrose, lactose, trehalose, D-sorbitol, D-mannitol, inositol, glycerin, starch and the like are all utilized. Neither acid nor gas is formed therefrom.

Alcaligenes N-81 is deposited in Fermentation Research Institute, Agency of Industrial Science and Technology, Japan as FERM-P No. 4368 and in American Type Culture Collection as ATCC 31369.

Bacteriological Properties of Alcaligenes N-243

(a) Morphology

Microscopic observation (cultured in a bouillon-agar medium at 30° C. for 48 hours)

(1) Shape and size of cell: It is a short rod having a size of 1–2×0.5 micron.
(2) Polymorphism of the cell: There is observed no polymorphism.
(3) Motility: Motile by means of one to several peritrichous flagella.
(4) Spore: It forms no spore.
(5) Gram-stain: Negative.
(6) Acid-fast: Negative.

(b) The State of Growth in Various Media:

(1) Bouillon-agar plate culture
When cultivated at 30° C. for 48 hours, it forms circular colonies having a diameter of 1–2 mm. The surface is flat and has convex round protrusions. The periphery is all-round. The colonies assume yellow with a gloss.

(2) Bouillon-agar slant culture
When cultivated at 30° C. for 48 hours, it shows a stringy medium growth. The surface is flat with yellow color and gloss.

(3) Bouillon submerged culture
In a standing culture at 30° C. for 48 hours, it forms slight turbidity with sediments.

(4) Bouillon-gelatin stab culture
In a standing culture at 20° C. for 42 days, it grows up to about 1 cm from the surface of medium without liquefaction of gelatin.

(5) Litmus milk culture
In a standing culture at 30° C. for 14 days, the medium becomes a little alkaline without coagulation of litmus milk.

(c) Physiological properties (1) Reduction of nitrates: Observed.
(2) Denitrification reaction: Slightly observed.
(3) MR test: Negative.
(4) VP test: Negative.
(5) Formation of indole: Not observed.
(6) Formation of hydrogen sulfide: Not observed.
(7) Hydrolysis of starch: Not observed.
(8) Utilization of citric acid: Observed. (Christensen medium is used.)
(9) Inorganic nitrogen source: Utilized. (Nitrates and ammonium salts)
(10) Formation of pigment: Not observed.
(11) Urease: Positive.
(12) Catalase: Negative.
(13) Growing condition range:
Temperature: 15°–40° C.
pH: 6.5–9.0
(14) Behavior to oxygen: Aerobic.
(15) O-F test (Hugh Leifson method): Negative.
(16) Utilization of carbon sources:
Carbon sources such as L-arabinose, D-xylose, D-glucose, D-mannose, D-fructose, D-galactose, maltose, sucrose, lactose, trehalose, D-sorbitol, D-mannitol, inositol, glycerin, starch and the like are all utilized. Neither acid nor gas is formed therefrom.

Alcaligenes N-243 is deposited in Fermentation Research Institute, Agency of Industrial Science and Technology, Japan as FERM-P No. 4369 and in American Type Culture Collection (ATCC) as ATCC 31370.

By comparing the above-mentioned characteristic bacteriological properties of Alcaligenes N-81 and Alcaligenes N-243 with the classification mentioned in "Bergey's Mannual of Determinative Bacteriology, 7th Ed. (1957) and 8th Ed. (1974)", a Judgement can be made that these two bacteria belong to Genus Alcaligenes in that they are negative with respect to gram-stain, they are motile by means of peritrichous flagella, they make litmus milk slightly alkaline and they are aerobic short bacilli.

Further, these two bacterial strains are regarded as analogous to *Alcaligenes faecalis* because they utilize nitrates and ammonium salts as only inorganic nitrogen sources, they form no indole and they utilize various carbon sources without formation of acid and gas at all. However, these two bacterial strains are different from *Alcaligenes faecalis* in that they form urease, and they hydrolyze urea. Thus, they are judged to be new strains belonging to Genus Alcaligenes.

In producing a methylguanidine-decomposing enzyme by use of the bacteria of this invention, conventional solid culture may be employed. It is more preferable, however, to employ liquid culture.

As the culture medium used in this invention, those used in the cultivation of bacteria belonging to Genus Alcaligenes may be employed. A preferable medium is obtained, for example, by adding at least one kind of inorganic salt such as manganese sulfate, manganese chloride, magnesium sulfate, magnesium chloride, ferrous sulfate, ferric sulfate, ferrous chloride, ferric chloride, phosphates and the like to at least one kind of organic or inorganic nitrogen source such as yeast extract, peptone, meat extract, corn steep liquor, steep liquor of soybean, steep liquor of wheat bran, ammonium sulfate, ammonium nitrate and the like and, if necessary, thereto adding appropriately a carbon source such as sugar, a vitamin, and the like.

If hydrochloride or sulfate of methylguanidine is added to the above-mentioned culture medium in an amount of about 0.01% (W/V) or more and preferably 0.1–1.0% (W/V) based on the total quantity of the medium, the yield of the methylguanidine-decomposing enzyme can be improved effectively.

The initial pH value of the medium is adjusted to about 6.5–9.0. The temperature of cultivation is 25°–37° C. and preferably about 30° C. The duration of cultivation is 10 hours or longer. It is preferable to carry out the cultivation aerobically by use of a liquid medium by the method of aeration spinner submerged culture, shaking culture or the like.

After completion of the cultivation, methylguanidine-decomposing enzyme is collected from the cultivated mixture, which can be carried out by the conventional means for collecting enzymes.

Since the enzyme of this invention is an enzyme existing in bacterial cells mainly, it is preferable to once separate the bacterial cells from the cultivated mixture by such a procedure as filtration, centrifugation or the like and then to collect the enzyme from the bacterial cells. Although the bacterial cells may be used as they are, it is more preferable to use them after destructing the bacterial cells by various destroying means such as ultrasonic disintegrator, French press, Dyno mill or the like or after dissolving the bacteiral cell wall by means of a cell wall solubilizing enzyme such as lysozyme.

The above-mentioned bacterial cells or their destructed products or products obtained by dissolving their cell wall are then extracted with water, buffer solution or an appropriate solvent. The extract may be used as it is as a crude enzyme solution. Otherwise, a crude enzyme powder is produced from the extract by an appropriately selected means such as freeze-drying, precipitation with alcohol, precipitation with acetone or the like. In obtaining a purified preparation of enzyme from the above-mentioned crude enzyme solution or crude enzyme powder, various methods such as gel filtration method using Sephadex or Biogel, adsorption-elution method using ion-exchanger, electrophoretic method using polyacrylamide gel, adsorption-elution method using hydroxyappatitie, sedimentation method such as sucrose density gradient centrifugation, affinity chromatography, and fractionating methods using molecular sieve, membrane, hollow thread membrane or the like are appropriately selected and combined, whereby a purified enzyme sample can be obtained.

By the following examples, this invention will be illustrated below more concretely in no limitative way.

EXAMPLE 1

2-liters of a culture medium (pH 7.2) comprising 1.0% (W/V) of glycerin, 0.2% (W/V) of methylguanidine sulfate, 0.1% (W/V) of disodium phosphate, 0.1% (W/V) of magnesium sulfate, 0.05% (W/V) of yeast extract, 0.01% (W/V) of ferrous sulfate, 0.01% (W/V) of manganese chloride and water was introduced into an agitated small-sized jarfermenter (manufactured by Iwashiya Co.) and sterilized in an autoclave. It was inoculated with 20 ml of a seed bacterial solution prepared by cultivating Alcaligenes N-243 (FERM-P No. 4396, ATCC 31370) in a medium having the same composition as above (pH 7.2) for 48 hours, and subjected to aeration spinner submerged culture at 30° C. for 48 hours.

The culture fluid thus obtained was centrifuged to give 17 g of wet bacterial cells. The resulting cells were destructed in the usual manner and then centrifuged to give 85 ml of a crude enzyme solution (enzyme activity: 27 units/ml) as supernatant.

The crude enzyme solution was salted out with ammonium sulfate in the usual manner. The precipitate formed at 55% saturation was separated by centrifugation, and subjected to gel filtration chromatography by passing it through a column packed with Sephadex G-200 which had been equilibrated with a small quantity of solution of KCl (0.1 M) in 0.01 M Tris-hydrochloric acid buffer solution (pH 8.0).

The active fraction thus obtained was passed through a column packed with DEAE-Sephacel which had been equilibrated with the same solution of KCl in Tris-hydrochloric acid buffer solution as above, and subjected to ion-exchange chromatography by using the same KCl solution in Tris-hydrochloric acid buffer solution as above till the quantity of eluate reached 120 ml and by the concentration gradient elution method at potassium chloride concentration of 0.2–0.4 M thereafter.

The active fraction thus obtained was adsorbed onto a column packed with hydroxyappatite. Using a 0.3 M solution of KCl in 0.01 M Tris-hydrochloric acid buffer solution (pH 8.0) till the quantity of eluate reached 200 ml, using 0.001 M phosphate buffer solution (pH 8.0) thereafter till the quantity of eluate reached 350 ml, using 0.005 M phosphate buffer solution (pH 8.0) thereafter till it reached 500 ml, using 0.01 M phosphate buffer solution (pH 8.0) thereafter till it reached 650 ml, using 0.03 M phosphate buffer solution (pH 8.0) thereafter till it reached 840 ml, using 0.05 M phosphate buffer solution (pH 8.0) thereafter till it reached 990 ml, using 0.07 M phosphate buffer solution thereafter till it reached 1120 ml, and using 0.1 M phosphate buffer solution (pH 8.0) thereafter, an active fraction of the enzyme was taken out.

The active fraction thus obtained was dialyzed against distilled water and freeze-dried to give 5 mg of a purified powder of the enzyme (enzyme activity: 46 units/mg).

EXAMPLE 2

10 ml of a culture medium (pH 7.2) comprising 1.0% (W/V) of glycerin, 0.4% (W/V) of methylguanidine sulfate, 0.1% (W/V) of disodium phosphate, 0.1% (W/V) of magnesium sulfate, 0.05% (W/V) of yeast extract, 0.01% (W/V) of ferrous sulfate, 0.01% (W/V) of manganese chloride and water was introduced into a large-sized test tube and sterilized in an autoclave. It was inoculated with one platinum loop quantity of Alcaligenes N-81 (FERM-P No. 4368, ATCC 31369) taken from stored slant, and subjected to shaking culture at 30° C. for 72 hours by means of a test tube shaker (manufactured by Iwashiya Co.).

The culture fluid thus obtained was centrifuged to collect the bacterial cells. The resulting cells were suspended in 4 ml of 0.05 M Veronal buffer solution (pH 9.0), and the cells were destructed for 10 minutes by means of an ultrasonic disintegrator (manufactured by Bronson Co.) while cooling with ice water. Then the precipitate was removed by centrifugation to give 3.8 ml of a crude enzyme solution (enzyme activity: 0.252 unit/ml) as supernatant.

EXAMPLE 3

Decomposition Test of Methylguanidine Test Procedure:

The crude enzyme solution obtained in Example 2 was salted out with ammonium sulfate in the usual manner and then dissolved into water to give an aqueous solution of methylguanidine-decomposing enzyme (67.2 units/ml).

50 μl of the aqueous solution thus obtained was added to 0.95 ml of a solution of methylguanidine sulfate in 0.1 M Tris-hydrochloric acid buffer solution having a methylguanidine sulfate concentration of 834 μg/dl (calculated concentration of methylguanidine: 500 μg/dl). The mixture was thoroughly stirred and then enzymatically reacted at 37° C. for 60 minutes while it was left standing. The quantities of methylguanidine before and after the enzymatic reaction were measured according to the method mentioned below. FIG. 4A illustrates the liquid chromatogram for sample before the enzymatic reaction, while FIG. 4B does the liquid chromatogram after the reaction.

The samples to be analyzed were prepared by adding 100 μl of 0.6 M perchloric acid to 100 μl of each sample, centrifuging the mixture at 8,000 r.p.m. for 10 minutes in the usual manner, and then adding 100 μl of 0.5 N solution of sodium hydroxide in 50% methanol to 100 μl of the deproteinized supernatant thus obtained.

The analysis of methylguanidine was carried out in accordance with the method mentioned on page 79 of the Synopsis of the 3rd Symposium on the Analytical Chemistry of Biological Components (Oct. 14, 1977, published by Japanese Pharmacological Society), except that the 0.15 M acetate buffer solution was replaced by 0.5 N solution of sodium hydroxide in 50% methanol, the 1 N solution of sodium hydroxide in 50% ethanol was replaced by 1 N aqueous solution of sodium hydroxide, and the 1 mM ethanolic solution of 9,10-phenanthraquinone was replaced by 0.2 mM solution of 9,10-phenanthraquinone in dimethylformamide. Results of the Measurement:

As shown in the liquid chromatogram of FIGS. 4A and 4B, a methylguanidine peak M was detected at an elution time of 12 minutes and 10 seconds in the sample which had been prepared by dissolving methylguanidine sulfate into 0.1 M Tris-hydrochloric acid buffer solution and was before the reaction with methylguanidine-decomposing enzyme (FIG. 4A), while no peak of methylguanidine was detected at the elution time of 12 minutes and 10 seconds in the sample after the reaction with the enzyme (FIG. 4B). Thus it has been revealed that methylguanidine can be decomposed and removed completely by reacting a methylguanidine-decomposing enzyme with a solution prepared by dissolving methylguanidine sulfate into 0.1 M Tris-hydrochloric acid buffer solution.

EXAMPLE 4

Test Procedure:

1 g of beef extract was diluted with water, pH was adjusted to 10.0 with sodium hydroxide, and the total volume was adjusted to 10 ml with water.

Figure 5B:
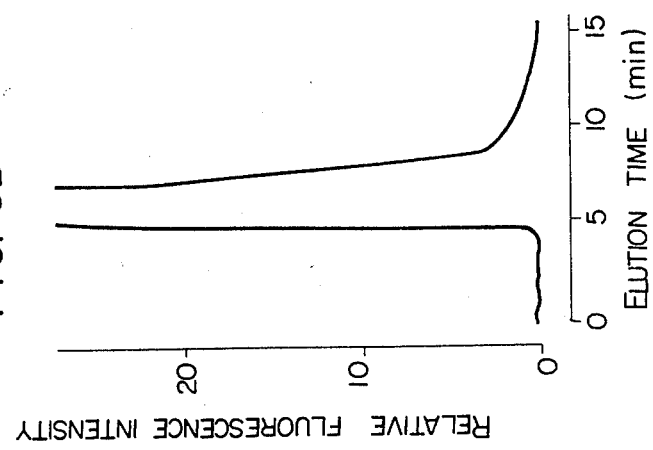
FIG. 5B illustrates the liquid chromatogram of an enzyme-treated product obtained by reacting a methylguanidine-decomposiing enzyme with a beef extract (after the enzymatic reaction), wherein M is the peak of methylguanidine.
Figure 5A:
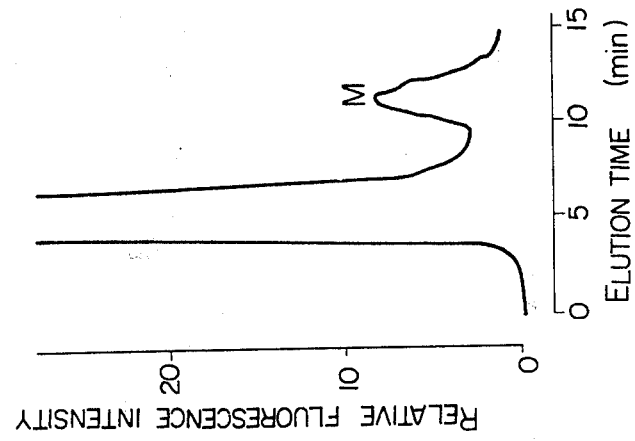
FIG. 5A is the liquid chromatogram of a beef extract (before the enzymatic reaction), wherein M is the peak of methylguanidine.

To 0.95 ml of the aqueous dilution of beef extract thus obtained, was added 50 μl of the aqueous solution of methylguanidine-decomposing enzyme used in Example 3 (67.2 units/ml). The mixture was thoroughly stirred and then enzymatically reacted at 40° C. for 20 minutes while it was left standing. The quantities of methylguanidine before and after the reaction were measured by the method mentioned in Example 3. FIG. 5A illustrates the liquid chromatogram before the enzymatic reaction and FIG. 5B does the liquid chromatogram after the reaction. Results of the Measurement:

As shown in the liquid chromatogram of FIGS. 5A and 5B, a methylguanidine peak M was detected at an elution time of 12 minutes and 10 seconds in the sample before the reaction with methylguanidine-decomposing enzyme (FIG. 5A), while no peak of methylguanidine was detected at the elution time of 12 minutes and 10 seconds in the sample after the reaction with the enzyme (FIG. 5B). Accordingly, it is understandable that methylguanidine can be decomposed and removed completely by reacting a methylguanidine-decomposing enzyme with beef extract.

EXAMPLE 5

Test Procedure:

25 g of smoked-dried bonito was sliced with a conventional slicer, mixed with 100 ml of hot water at 60° C. and homogenized for 5 minutes by means of a homogenizer.

The homogenized product was extracted with stirring at 50° C. for 30 minutes, the residue of extraction was filtered off with suction, and there was obtained a hot water extract of smoked-dried bonito (pH: 6.1).

Figure 6B:
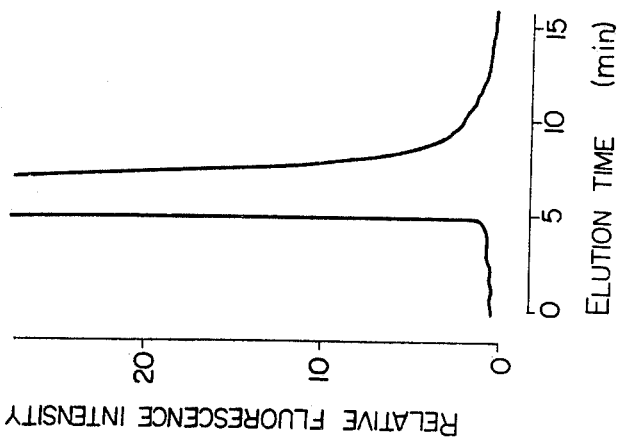
FIG. 6B illustrates the liquid chromatogram of an enzyme-treated product obtained by reacting a methylguanidine-decomposing enzyme with a hot water extract of smoked-dried bonito (after the enzymatic reaction).
Figure 6A:
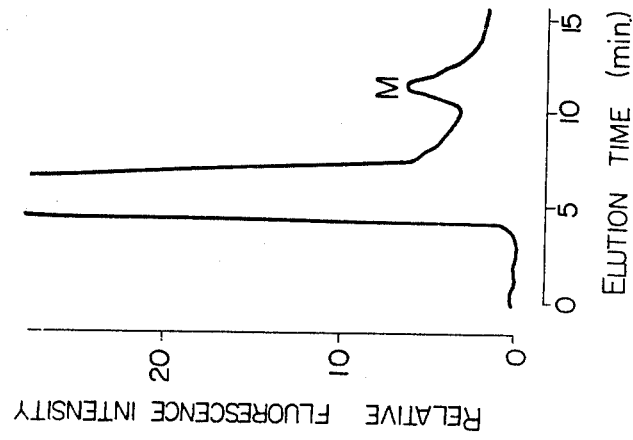
FIG. 6A illustrates the liquid chromatogram of a hot water extract of smoked-dried bonito (before the enzymatic reaction), wherein M is the peak of methylguanidine.

Then the extract was mixed with 1 ml of the aqueous solution of methylguanidine-decomposing enzyme used in Example 3 and enzymatically reacted at 5° C. for 18 hours while it was left standing. The quantities of methylguanidine before and after the reaction were measured by the method mentioned in Example 3. FIG. 6A illustrated the liquid chromatogram before the enzymatic reaction and FIG. 6B does the liquid chromatogram after the reaction. Results of the Measurement:

As shown in the liquid chromatogram of FIGS. 6A and 6B, a methylguanidine peak M was detected at an elution time of 12 minutes and 10 seconds in the sample of hot water extract of smoked-dried bonito, before being reacted with methylguanidine-decomposing enzyme (FIG. 6A), while no peak of methylguanidine was detected at the elution time of 12 minutes and 10 seconds in the sample after being reacted with the enzyme (FIG. 6B). It is understandable, accordingly, that methylguanidine can be decomposed and removed completely by reacting a methylguanidine-decomposing enzyme with hot-water extract of smoked-dried bonito.

EXAMPLE 6

Preparation of Fixed Enzyme:

The aqueous solution of enzyme obtained in Example 3 was sufficiently dialyzed at 4° C. against 0.1 M sodium carbonate-sodium bicarbonate buffer solution (pH 10.0) containing 0.5 M sodium chloride to give an enzyme solution having an enzyme activity of 63.8 units/ml. To 10 ml of the solution thus obtained, was added 1 g of activated CH-Sepharose 4B (carrier, manufactured by Pharmacia Co., Ltd.) swollen with 0.001 M hydrochloric acid.

Then the mixture was reacted at 20° C. for 2 hours with gentle stirring, whereby the methylguanidine-decomposing enzyme was combined to the carrier. The resulting product was washed with the same buffer solution as above, suspended in 1 M solution of ethanolamine (pH 8.0) and allowed to stand at 25° C. for 2 hours, and then it was filtered by means of a glass filter.

The product collected by the filtration was washed with 0.1 M acetate buffer solution (pH 6.2) and then with 0.1 M Tris-hydrochloric acid buffer solution (pH 7.4) to give a fixed enzyme (212 units/g). Test Procedure:

0.2 g of the above-mentioned fixed enzyme was added to 1 ml of a serum of uremic patient (methylguanidine concentration 196 μg/dl; pH 7.4), and the mixture was enzymatically reacted at 37° C. for 30 minutes with gentle stirring. The enzymatic reaction was stopped by filtering off the fixed enzyme.

Figure 7A:
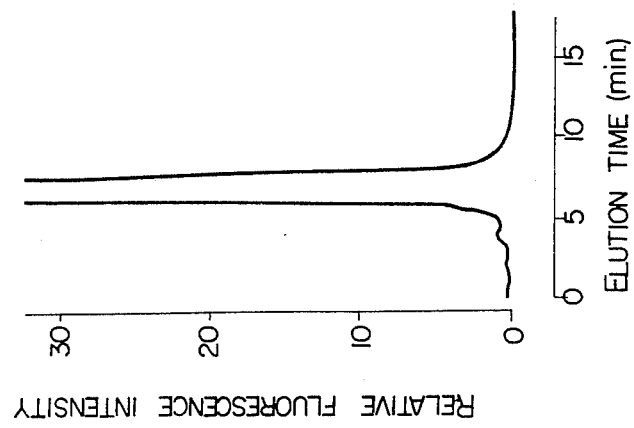
FIG. 7A illustrates the liquid chromatogram of the serum of a uremic patient (before the enzymatic reaction), wherein M is the peak of methylguanidine.
Figure 7B:
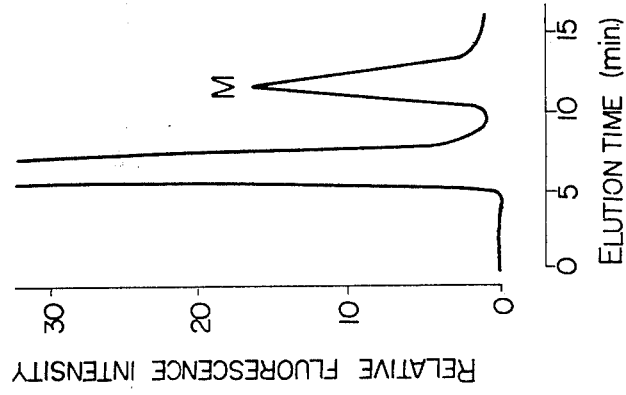
FIG. 7B illustrates the liquid chromatogram of an enzyme-treated product obtained by reacting a methylguanidine-decomposing enzyme with a serum of uremic patient (after the enzymatic reaction).

The quantities of methylguanidine before and after the enzymatic reaction were measured according to the method mentioned in Example 3. FIG. 7A illustrates the liquid chromatogram before the enzymatic reaction, while FIG. 7B does the liquid chromatogram after the reaction. Results of the Measurement:

As shown in the liquid chromatogram of FIGS. 7A and 7B, a peak of methylguanidine M was detected at an elution time of 12 minutes and 10 seconds in the serum of uremic patient before being reacted with the methylguanidine-decomposing enzyme (FIG. 7A), whereas no peak of methylguanidine was found at the elution time of 12 minutes and 10 second in the sample after being reacted with the enzyme (FIG. 7B). It is understandable, accordingly, that methylguanidine can be decomposed and removed completely by reacting a methylguanidine-decomposing enzyme with the serum of uremic patient.

EXAMPLE 7

1 g of beef extract (manufactured by DIFCO Co.) was mixed with 1 ml of 1 N sodium hydroxide solution, to which was further added 0.05 M sodium carbonate-sodium bicarbonate buffer solution (pH 10.0) to dissolve the beef extract completely. The total volume was adjusted to 10 ml with the buffer solution.

0.9 ml of the solution thus obtained was thoroughly mixed with 100 μl of the methylguanidine-decomposing enzyme solution mentioned in Experimental Example 1, and the resulting mixture was reacted at 37° C. for 30 minutes while it was left standing. Then the reaction mixture was thoroughly mixed with 200 μl of 1 N phosphoric acid and 0.8 ml of 0.05 M phosphate buffer solution (pH 6.6). In accordance with the urease-indophenol method mentioned in Experimental Example 1, 200 μl of reagent A was added to 200 μl of the above-mentioned mixture, and then it was treated in just the same manner as mentioned in Experimental Example 1 for the sake of measuring O. D. value. Thus, the O. D. value was found to be 0.898.

The blank was measured by repeating the procedure mentioned above, except that the 100 μl of methylguanidine-decomposing enzyme solution was used after being treated in a boiling water bath at 100° C. for 5 minutes. The blank O. D. value was found to be 0.774.

Then, the quantity of methylguanidine was determined by applying the residual O. D. value, obtained by deducting the blank O. D. value from the found O. D. value, to the standard calibration curve obtained in Experimental Example 1. Thus, it was found that 200 μl of the beef extract contained 0.011 micromole of methylguanidine and the content of methylguanidine was 89.3 μg per 1 g of the beef extract.

What is claimed is:

1. A methylguanidine-decomposing enzyme which has an ability to decompose methylguanidine into methylamine and urea, has an optimum pH range of 10.9–12.3 and has a stable pH range of 5.0–10.6.

2. A process for removing methylguanidine from samples containing methylguanidine which comprises adding the methylguanidine-decomposing enzyme which has an ability to decompose methylguanidine into methylamine and urea, has an optimum pH range of 10.9–12.3 and has a stable pH range of 5.0–10.6.

3. A process according to claim 2, wherein said sample containing methylguanidine is at least one member selected from the group consisting of extracts of chicken, beef, whale meat, pork, and fish meat; smoked-dried bonito, mackerel, and round herring; and the blood of uremic patients.

4. A process according to claim 2, wherein the enzymatic decomposition is carried out at a temperature of 80° C. or below.

5. A method for quantitatively analyzing methylguanidine in sample which comprises reacting the methylguanidine-decomposing enxyme of claim 2 with the sample to be analyzed for methylguanidine and measuring the quantity of methylamine or urea formed by the reaction.

6. A method according to claim 5, wherein said sample is at least one member selected from the group consisting of meat extracts, smoked-dried fishes, bloods, sera and urines.

7. A method according to claim 5, wherein the enzymatic decomposition is carried out at a temperature of 80° C. or below.

8. A process for producing the methylguanidine-decomposing enzyme of claim 1 which comprises cultivating a bacterium belonging to Genus Alcaligenes and having an ability to produce methylguanidine-decomposing enzyme in a medium and collecting the formed methylguanidine-decomposing enzyme from the cultivated mixture.

9. A process according to claim 8, wherein the cultivation is carried out in a medium containing methylguanidine sulfate or hydrochloride in an amount of 0.01% (W/V) or more based on the total quantity of the medium.

10. A process according to claim 8, wherein the cultivation is carried out at a temperature of 25°–37° C. for a time period of 10 hours or more by the method of liquid culture.

11. A process according to claim 8, wherein said bacterium belonging to Genus Alcaligenes is Alcaligenes N-81 (ATCC 31369, FREM-P No. 4368) or Alcaligenes N-243 (ATCC 31370, FERM-P No. 4369).

* * * * *